United States Patent
Cooke et al.

(10) Patent No.: US 6,605,115 B1
(45) Date of Patent: Aug. 12, 2003

(54) METHOD AND COMPOSITION FOR INHIBITING CARDIOVASCULAR CELL PROLIFERATION

(75) Inventors: John P. Cooke, Palo Alto, CA (US); Garrison C. Fathman, Portola Valley, CA (US); Jonathan B. Rothbard, Woodside, CA (US); Shiro Uemura, Nara (JP); Robert C. Robbins, Stanford, CA (US); Murray H. Kown, Menlo Park, CA (US)

(73) Assignee: Board of Trustees of the Leland Stanford Junior University, Stanford, CA (US)

( * ) Notice: Subject to any disclaimer, the term of this patent is extended or adjusted under 35 U.S.C. 154(b) by 14 days.

(21) Appl. No.: 09/587,647

(22) Filed: Jun. 5, 2000

Related U.S. Application Data
(60) Provisional application No. 60/137,826, filed on Jun. 5, 1999.

(51) Int. Cl.$^7$ .................................................. A61F 2/06
(52) U.S. Cl. ..................................... 623/1.48; 623/1.42
(58) Field of Search ............................... 623/1.48, 1.42; 128/898; 427/2.24, 2.25

(56) References Cited

U.S. PATENT DOCUMENTS

| | | | |
|---|---|---|---|
| 5,032,608 A | * 7/1991 | Dudrick | 514/396 |
| 6,231,847 B1 | * 5/2001 | Bisgaier et al. | 424/78.08 |
| 6,365,338 B1 | * 4/2002 | Bull et al. | 435/1.1 |
| 6,425,881 B1 | * 7/2002 | Kaesemeyer | 604/93.01 |

FOREIGN PATENT DOCUMENTS

| | | | | |
|---|---|---|---|---|
| US | WO98/52614 | * 11/1998 | | A61K/47/48 |
| WO | WO 98/52614 | 11/1998 | | |

OTHER PUBLICATIONS

Cardiac Surgery Homepage, "Coronary Bypass Surgery", Dec. 1998, http://heart-surgeon.com/coronary-bypass.html.*

Cooke, J.P. and Dzau, V.J., "Nitric oxide synthase: Role in the Genesis of Vascular Disease" *Annu. Rev. Med.* 48:489–509 (1997).

Dattilo, J.B., et al., "Inducible Nitric Oxide Synthase Expression in Human Vein Grafts" *Am J Surg.* 174:177–180 (1997).

Garg, U.C. and Hassid, A., "Nitric Oxide-generating Vasodilators and 8-Bromo-Cyclic Guanosine Monophosphate Inhibit Mitogenesis and Proliferation of Cultured Rat Vascular Smooth Muscle Cells" *J. Clin. Invest.* 83:1774–1777 (1989).

Lloyd-Jones, D.M. and Bloch, K.D., "The vascular biology of nitric oxide and its role in atherogenesis" *Annu. Rev. Med.* 47:365–375 (1996).

Tsao, P.S., et al., "Nitric Oxide Regulates Monocyte Chemotactic Protein–1" *Circulation* 96:934–940 (1997).

Wolf, A., et al., "Dietary L-Arginine Supplementation Normalizes Platelet Aggregation in Hypercholesterolemic Humans" *JACC* 29(3):479–485 (1997).

Thomas, G., et al., "Vascular activity of polycations and basic amino acids: L-arginine does not specifically elicit endothelium-dependent relaxation" *Biochemical and Biophysical Research Communications* 158(1):177–180 (1989).

* cited by examiner

*Primary Examiner*—Corrine McDermott
*Assistant Examiner*—Thomas Barrett
(74) *Attorney, Agent, or Firm*—Reed & Eberle LLP; Dianne E. Reed; Shelley P. Eberle

(57) ABSTRACT

Cardiovascular cell proliferation in a blood vessel subjected to trauma, such as angioplasty, vascular graft, anastomosis, or organ transplant, can be inhibited by contacting the vessel with a polymer consisting of from 6 to about 30 amino acid subunits, where at least 50% of the subunits are arginine, and the polymer contains at least six contiguous arginine subunits. Exemplary polymers for this purpose include arginine homopolymers 7 to 15 subunits in length.

28 Claims, 10 Drawing Sheets

METHOD AND COMPOSITION FOR INHIBITING CARDIOVASCULAR CELL PROLIFERATION

This application claims priority to U.S. provisional application serial No. 60/137,826, filed Jun. 5, 1999, which is hereby incorporated by reference in its entirety.

STATEMENT OF GOVERNMENT INTEREST

This invention was made with the support of NIH grant number CA 65237. Accordingly, the U.S. Government may have certain rights in this invention.

FIELD OF THE INVENTION

The present invention relates to methods and compositions for inhibiting cardiovascular cell proliferation. The invention provides methods for improving the longevity and quality of arterial grafts, for enhancing vascular NO production, and for reducing post-graft intimal hyperplasia, stenosis, and restenosis.

References

Best, P. J. et al., Arterioscler. Thromb. Vasc. Biol. 19:14–22 (1999).
Boger, R. H. et al., "Asymmetric Dimethylarginine (ADMA): A Novel Risk Factor for Endothelial Dysfunction. Its Role in Hypercholestrolemia", Circulation 98:1842–1847 (1998).
Cooke, J. P. and Dzau, V. J., "Nitric Oxide Synthase: Role in the Genesis of Vascular Disease", Ann. Rev. Med. 48:489–509 (1997).
Cooke, J. P. et al., Ann. Rev. Med. 48:489–509 (1997).
D'Aniello, A. et al., "Further Study on the Specificity of D-Amino Acid Oxidase and D-Aspartase Oxidase and Time Course for Complete Oxidation of D-Amino Acid", Comp. Biochem. Physiol.[B] 105: 731–734 (1993).
Dattilo, J. B. et al., "Inducible Nitric Oxide Synthase Expression in Human Vein Grafts", Am. J. Surg. 174:177–180 (1997).
Demeyer, G. R. Y. and Bult, H., "Mechanisms of Neointima Formation—Lessons from Experimental Models", Vasc. Med. 2:179–189 (1997).
Deves, R. and Boyd, C. A., "Transporters for Cationic Amino Acids in Animal Cells: Discovery, Structure, and Function", Physiol. Rev. 78:485–545 (1998).
Edelman, E. R. et al., Circ. Res. 76(2):176–182 (1995).
Garg, U. C. and Hassid, A., "Nitric Oxide-Generating Vasodilators and 8-Bromocyclic Guanosine Monophosphate Inhibit Mitogenesis and Proliferation of Cultured Rat Vascular Smooth Muscle Cells", J. Clin. Invest. 83(5):1774–7 (May 1989).
Guoyao, W. U. and Morris, S. M. "Arginine Metabolism: Nitric Oxide and Beyond", Biochem. J. 366:1–17 (1998).
Hansson, G. K. et al., "Arterial Smooth Muscle Cells Express Nitric Oxide Synthase in Response to Endothelial Injury", J. Exp. Med. 180:733–738 (1994).
Harrison, D. G., "Cellular and Molecular Mechanisms of Endothelial Cell Dysfunction" J. Clin. Invest. 100:2153–2157 (1997).
Hill, C. M. et al., "Exploration of Requirements for Peptide Binding to HLA DRB1.0101 and DRB1.0401", J. Immunol. 152:2890–2895 (1994).
Himmelfarb, J., Curr. Opin. Nephrol. Hypertens. 8(5):569–72 (September 1999).
Isselhard, W. et al., Thoracic and Cardiovascular Surg. 28(5):329–36 (1980).
Kraiss, L. W. et al., "Response of the Arterial Wall to Injury and Intimal Hyperplasia", in The Basic Science of Vascular Disease, Sumpio et al., Eds., Futura Publishing, NY, N.Y., Pp.289–317 (1997).
Lloyd, J. D. and Bloch, K. D., "The Vascular Biology of Nitric Oxide and its Role in Atherogenesis", Ann. Rev. Med. 47:365–375 (1996).
Morris, S. M. and Billiar, T. R., "New Insights into the Regulation of Inducible Nitric Oxide Synthesis", Am. J. Physiol. 266:E829–E839 (1994).
Motwani, J. G. et al., Circulation 97:916–931 (1998).
Nagase, S. et al., "A Novel Nonenzymatic Pathway for Generation of Nitric Oxide by the Reaction of Hydrogen Peroxide and D- or L-Arginine", Biochem. Biophys. Res. Commun. 233:150–153 (1997).
Radomski, M. W. et al. "An L-Arginine/Nitric Oxide Pathway Present in Human Platelets Regulates Aggregation", Proc. Natl. Acad. Sci. USA 87:5193–5197 (1990).
Tsao, P. S. et al., "Fluid Flow Inhibits Endothelial Adhesiveness. Nitric Oxide and Transcriptional Regulation of VCAM-1", Circulation 94:1682–1689 (1996).
Tsao, P. S. et al., "Nitric Oxide Regulates Monocyte Chemotactic Protein-1", Circulation 96:934–940 (1997).
Wang, Q. et al., "The in vivo Unidirectional Conversion of Nitro-D-Arginine to Nitro-L-Arginine", J. Pharmacol. Exp. Ther. 288:270–273 (1999).
Wolf, A. et al., "Dietary L-Arginine Supplementation Normalized Platelet Aggregation in Hypercholesterolemic Humans", J. Am. Coll. Cardiol. 29:479–485 (1997).
Woods, J. D. and Port, F. K., Nephrol. Dial. Transplant. 12(4):657–9 (April 1997).

BACKGROUND OF THE INVENTION

Myointimal hyperplasia is a vascular response to injury that contributes to the development of vein graft disease, restenosis after angioplasty, and atherosclerosis (Motwani et al., 1998). Myointimal hyperplasia involves the migration and proliferation of vascular smooth muscle cells (VSMC) as well as the elaboration of extracellular matrix in the intima (DeMeyer et al., 1997; Kraiss et al., 1997). Vascular nitric oxide (NO), an endogenous regulator of vascular function, opposes the development of myointima formation by inhibiting VSMC proliferation and by inducing VSMC apoptosis (Cooke et al., 1997; Best et al., 1999). Failure of endogenous biological processes to control myointimal hyperplasia can lead to formation of vascular occlusions which seriously compromise tissue function.

Autologous vein grafting constitutes a major tool in coronary bypass procedures. About 400,000 to 500,000 first-time coronary graft procedures are performed every year in the United States alone. Although patient survival rates exceed 90% over the first five years after treatment, about 20% to 40% of the grafts fail during this time due to occlusive phenomena. Thus, 80,000–100,000 graft replacement procedures are needed in the U.S. yearly to avoid premature mortality. Vascular occlusive phenomena also lead to failures in other vascular grafts, such as arterial-venous anastomosis used for kidney dialysis, and in organ transplants.

In light of the significant costs to patients and insurers engendered by repeated graft procedures, there is a need to improve the longevity and quality of first-time vascular grafts. Ideally, such a procedure should be simple to carry out, without requiring extensive manipulation or lengthy processing. Furthermore, the procedure preferably involves materials that are relatively easy to prepare in therapeutically effective forms.

SUMMARY OF THE INVENTION

In one aspect, the invention provides a method for inhibiting trauma-induced intimal hyperplasia in a blood vessel. In accordance with the method, a polymer consisting of from 6 to about 30 amino acid subunits, wherein at least 50% of the subunits are arginine, and containing at least six contiguous arginine subunits, contained in a pharmaceutically acceptable vehicle, is contacted with the vessel, typically with the interior of the vessel. Such contacting is effective to reduce the level of intimal hyperplasia in and/or adjacent to the vessel, relative to the level of intimal hyperplasia that would occur in the absence of the contacting.

The hyperplasia-inducing trauma may comprise an incision to the vessel, excessive or prolonged pressure applied to the vessel, transplant of an organ containing the vessel, or a combination thereof. The contacting may occur prior to the trauma (as in preparation of a vessel segment for grafting), concurrent with, or following the trauma (as in an angioplasty procedure). The vessel may be a vessel conduit to be grafted into (as in a bypass procedure) or onto (as in an anastomosis) an endogenous vessel, or it can be an endogenous vessel receiving a graft. Also included are vein "patches" used in arterial repair. In preferred embodiments, the above noted procedures take place in a human subject.

The invention provides, for example, a method for repairing an arterial vessel site in a human subject. Accordingly, an isolated vessel conduit, such as a saphenous vein segment or an internal mammary artery segment, is contacted with a polymer as described above, in a pharmaceutically acceptable vehicle, and the vessel conduit is then grafted into a selected arterial vessel site in need of repair.

In one embodiment, the vessel is a vein which undergoes an arterial venous anastomosis procedure for the purpose of dialysis. In another embodiment, the vessel is subjected to angioplasty. In a further embodiment, the vessel is contained within a transplanted organ, such as, for example, a heart or kidney, where the contacting is preferably carried out by immersion of the organ in a solution of the polymer.

Preferably, at least 70%, and more preferably at least 90%, of the subunits in the polymer are arginine. When non-arginine subunits are present, preferably no arginine subunit is separated from another arginine subunit by more than one non-arginine subunit. The non-arginine subunits are preferably amino acid subunits which do not significantly reduce the rate of membrane transport of the polymer. In preferred embodiments, the arginine subunits are L-arginine. In particularly preferred embodiments, the polymer is an arginine homopolymer, preferably containing 7 to 15 arginine residues.

Also provided is an isolated vessel conduit, comprising, within the wall of the conduit, a polymer as described above, present at a level effective to reduce the level of post-graft intimal hyperplasia in and/or adjacent to the conduit, relative to the level of post-graft intimal hyperplasia that would occur in the absence of the polymer. The vessel conduit may be a venous or arterial segment, or it may be an artificial vessel segment made from a physiologically compatible material.

The invention also provides a method of preparing a vascular conduit for a vascular graft procedure, wherein an isolated vessel conduit, preferably the interior of the conduit, is contacted with a an arginine polymer as described above, in a pharmaceutically acceptable vehicle, for a time sufficient for the polymer to be transported into the wall of the vessel conduit to a level effective to reduce post-graft intimal hyperplasia in and/or adjacent to the conduit, relative to the level of post-graft intimal hyperplasia that would occur in the absence of such contacting with the polymer. Preferred embodiments of the polymer are as described above.

The invention also provides a method of increasing NO production in a vascular cell or tissue, by contacting a polymer consisting of from 6 to about 30 amino acid subunits, wherein at least 50% of the subunits are L-arginine, and containing at least six contiguous arginine subunits, in a pharmaceutically acceptable vehicle, with the cell or tissue.

In vascular tissue, the polymers as described above are shown to translocate through the vascular wall and into the cytoplasm and nuclei of vascular cells. In addition to their utility in inhibiting myointimal hyperplasia, the oligomers are useful as transporters of vascular therapeutics.

These and other objects and features of the invention will become more fully apparent when the following detailed description of the invention is read in conjunction with the accompanying drawings.

BRIEF DESCRIPTION OF THE DRAWINGS

FIG. 1A) and biotin-labeled heptaarginine (bR7) at 0.1 $\mu$M (FIG. 1B) and 10 $\mu$M (FIG. 1C). Note intense staining in the nuclei and cytoplasm of all cells in FIGS. 1B–C. FIG. 1D shows bR7 translocation at 4° C.; there is no apparent reduction in efficacy of transport at this temperature. FIG. 1E shows inhibition of bR7 translocation by sodium azide, indicating that the transport process is energy-dependent. FIG. 1F shows lack of inhibition of bR7 translocation by addition of 10 mM free L-arginine to the medium, indicating that the y+ transporter is not involved in polymer uptake.

In FIGS. 4–7, extracellular NO production was measured as its stable oxidative metabolite, $NO_2$. (a) Effect of IFN-$\gamma$ dose on NO production by rat VSMC, incubated in medium containing 400 $\mu$M free L-arginine, stimulated with a mixture of IFN-$\gamma$ (100 U/ml) and LPS (100 $\mu$g/ml). (b) Effect of extracellular free L-arginine on NO production. $NO_2$ accumulation in the culture medium was quantified after 24 hours. $NO_2$ production was corrected as $10^5$ cells.

FIG. 5 shows the effect of arginine oligomers on NO synthesis in cytokine-stimulated VSMC. VSMCs were pretreated with arginine oligomers for 30 minutes, and then stimulated with a mixture of IFN-γ (100 U/ml) and LPS (100 μg/ml). NO production is expressed as a percentage of that observed in vehicle treated cytokine-stimulated cells. R5, penta-L-arginine; R7, hepta-L-arginine; R9, nona-L-arginine; D-r7, hepta-D-arginine; K7, hepta-L-lysine. *; $p<0.05$ vs. vehicle treated cells.

FIG. 6 shows the effect of N-terminal acetylation of the arginine oligomers on NO production. Rat VSMCs were pretreated with each polymer for 30 minutes, then stimulated with a mixture of IFN-γ (100 U/ml) and LPS (100 μg/ml). NO production is expressed as a percentage of that observed in vehicle treated cytokine-stimulated cells. *; $p<0.05$ vs. vehicle treated cells.

FIG. 7 shows the effect of L-NMMA on NO production from arginine oligomer treated VSMC. NO production is expressed as a percentage of that observed in vehicle treated cytokine-stimulated cells. *; $p<0.05$ vs. vehicle treated cells.

DETAILED DESCRIPTION OF THE INVENTION

I. Definitions

Figure 1A:
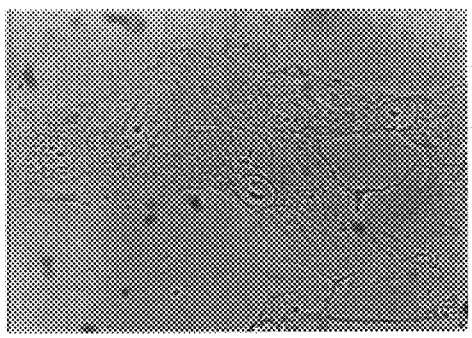
FIGS. 1A–F show translocation of biotin labeled heptaarginine (R7) into cultured rat vascular smooth muscle cells (VSMC). Each figure is representative of three separate experiments. The cells were treated for 30 minutes with with biotin-labeled heptalysine (bK7; 10 $\mu$M.
Figure 1B:
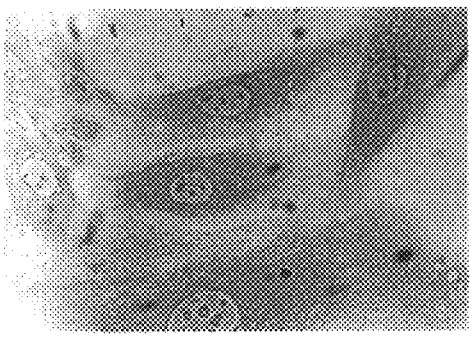
Figure 1C:
Figure 1D:
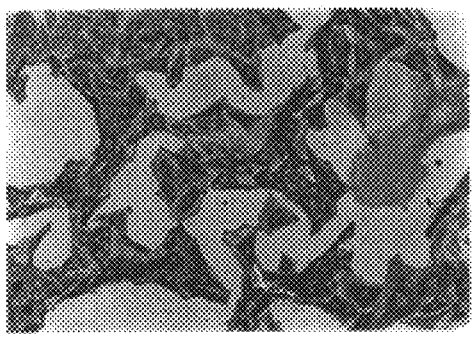
Figure 1E:
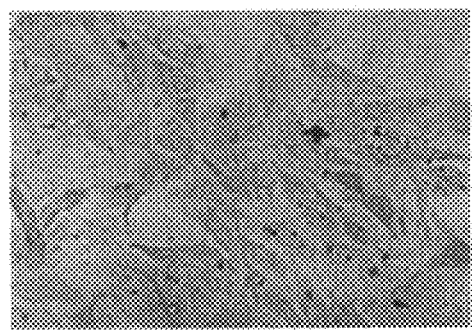

The term "poly-arginine" or "poly-Arg" refers to a polymeric sequence composed of contiguous arginine residues; poly-L-arginine refers to all L-arginines; poly-D-arginine refers to all D-arginines. Poly-L-arginine is also abbreviated by an upper case "R" followed by the number of L-arginines in the peptide (e.g., R8 represents an 8-mer of contiguous L-arginine residues). Poly-D-arginine is abbreviated by a lower case "r" followed by the number of D-arginines in the peptide (r8 represents an 8-mer of contiguous D-arginine residues). "Ac" indicates a sequence having an acetylated N-terminal residue (e.g. AcR7), while "b" indicates a sequence having a biotinylated N-terminal residue (e.g. bR7).

An "arginine polymer" (or "oligomer"), as used herein, refers to an arginine homopolymer or a peptide copolymer in which arginine is the major component (at least 50%, preferably at least 70%, and more preferably at least 90% arginine). An "arginine homopolymer", wherein all residues are arginine, may contain a mixture of L-arginine and D-arginine residues.

A "vessel" as used herein refers to a blood vessel or any segment thereof, including a segment used as a vascular patch.

Amino acid residues are referred to herein by their full names or by standard single-letter or three-letter notations: A, Ala, alanine; C, Cys, cysteine; D, Asp, aspartic acid; E, Glu, glutamic acid; F, Phe, phenylalanine; G, Gly, glycine; H, His, histidine; I, Ile, isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; Y, Tyr, tyrosine.

II. Arginine Polymers

The present invention utilizes arginine homopolymers, or copolymers having arginine as their major component, that are efficiently transported into vascular tissues, and that reduce intimal hyperplasia when treated vessel segments, such as arterial segments, venous segments, or artificial vessel conduits, are grafted into vascular sites in need of repair. The polymers are also useful in reducing post-transplant hyperplasia, such as GCAD (graft coronary artery disease), and inhibiting intimal hyperplasia in vein segments used as "patches", e.g. for arterial walls damaged during edarterectomy for atherosclerotic plaques. The polymers are also useful for reducing hyperplasia in vessels subjected to high pressures, as in angioplasty or blood dialysis.

The arginine polymer or copolymer contains at least 6, more preferably at least 7, and up to 30 amino acid residues, where at least 50% of these residues are arginine, and at least 6 contiguous residues are arginine. Preferably, at least 70%, and more preferably at least 90%, of the residues are arginine. Non-arginine residues, if present, are amino acid subunits (including unnatural amino acids) which do not significantly reduce the rate of membrane transport of the polypeptide. These are preferably selected from the group consisting of glycine, alanine, cysteine, valine, leucine, isoleucine, methionine, serine, and threonine, and more preferably selected from the group consisting of glycine, alanine, cysteine, and valine. Non-naturally occurring amino acids which are homologs of arginine may also be used. These include α-amino-β-guanidinopropionic acid, α-amino-γ-guanidinobutyric acid, or α-amino-ε-guanidinocaproic acid (containing 2, 3 or 5 linker atoms, respectively, between the backbone chain and the central guanidinium carbon).

In a preferred embodiment, all of the residues are arginine. In further embodiments, the polymer is an arginine homopolymer containing 6 to 25, more preferably 6 to 15, and most preferably 7 to 10 arginine residues. The arginine residues may be L-stereoisomers, D-stereoisomers, or a combination thereof. Preferably, all of the arginine residues have the L-configuration.

The terminal ends of the arginine polymer can be capped or uncapped. Preferably, the terminal ends are uncapped, meaning that the N-terminus has a free amino group and the C-terminus has a free carboxylic acid. However, the polymer can be capped at either or both terminal ends with selected terminal moieties, if desired, provided that the capping groups do not adversely affect the therapeutic benefits of the polymer. For example, the N-terminus can be capped with an N-acetyl, N-methyl, N-dimethyl, N-ethyl, N-diethyl, N-Boc, N-benzyl group, or the like. Similarly, the C-terminus can be capped with an amino group of the form $NR_2$ (free amino, alkylamino, or dialkylamino) to form a terminal amide moiety ($CONR_2$), wherein each R group is separately H or a linear, cyclic or branched $C_1$–$C_{10}$ alkyl group, preferably $C_1$–$C_5$ alkyl, and more preferably $C_1$–$C_2$ alkyl); or an alkyl alcohol of the form OR, to form a carboxylic acid ester ($CO_2R$), wherein R is a linear, cyclic or branched $C_1$–$C_{10}$ alkyl group, preferably $C_1$–$C_5$ alkyl, and more preferably $C_1$–$C_2$ alkyl, or the like. Preferably, such N- and C-capping groups contain no more than 20 carbon atoms, and preferably no more than 10 carbon atoms.

In one embodiment, the polymer has the formula X-$Arg_n$-Y, wherein X is $NH_2$ or an N-terminal capping group, Y is $COO^-$ or a C-terminal capping group, and n is an integer from 6 to 30, such that the Arg residues are L-arginine residues, D-arginine residues, or combinations thereof. In selected embodiments, n is an integer from 6 to 30, 7 to 30, 6 to 25, 7 to 25, 6 to 15, 7 to 15, 6 to 10, or 7 to 10. Preferably, the arginine residues all have an L-configuration.

The polymers formula also include all protonated variants that may occur, with associated counterions. The arginine polymer may be provided as a pharmaceutically acceptable salt with one or more counterions, such as phosphate, sulfate, chloride, acetate, propionate, fumarate, maleate, succinate, citrate, lactate, palmitate, cholate, mucate, glutamate, camphorate, glutarate, phthalate, tartrate, laurate, stearate, salicylate, methanesulfonate, benzenesulfonate, sorbate, picrate, benzoate, cinnamate, and the like.

The arginine polymers can be prepared by any method available in the art. Conveniently, the polymers are produced synthetically, e.g., using a peptide synthesizer (PE Applied Biosystems Model 433) (See Example 1), or they can be synthesized recombinantly using a biological expression system by methods well known in the art.

For use in transport of biological agents, the polymers of the invention may be conjugated to compounds to be transported, by methods known in the art. Exemplary methods of synthesis, including incorporation of cleavable linkers, exemplary classes of biological agents to be transported, and methods and formulations for administration, are described in copending and co-owned application Ser. No. 09/083,259, entitled "Method and Composition for Enhancing Transport Across Biological Membranes", which is incorporated herein by reference in its entirety.

III. Transport of Arginine Polymers Across Vascular Cell Membranes

In the studies described below, transmembrane transport and cellular uptake of oligomers was assessed by incubating cells or tissue with biotin-oligomer conjugates, followed by treatment with horseradish peroxidase (HRP)-conjugated streptavidin and subsequent incubation with DAB (3,3'-diaminobenzidine), a substrate of the enzyme which produces a highly colored product.

A. Translocation of Arginine Polymers into Cultured VSMC and Endothelial Cells

Cultured VSMC (vascular smooth muscle cells) were treated, as described in Example 2, with biotinylated oligomers of arginine or lysine. After incubation, the cells were treated with HRP-streptavidin conjugate, then with DAB. Staining by the oxidation product was observed using light microscopy.

Results are shown in FIG. 1. With polylysine (bK7; 10 $\mu$M), no internalized biotin signal was observed (FIG. 1A). On the other hand, even at the lowest concentration of biotinylated heptaarginine (bR7; 0.1 $\mu$M), internalized biotin was observed in all VSMCs (FIG. 1B). Incubation with 10 $\mu$M bR7 showed very intense staining, not only in the cytoplasm, but also in the nucleus of all VSMC (FIG. 1C).

Figure 1F:
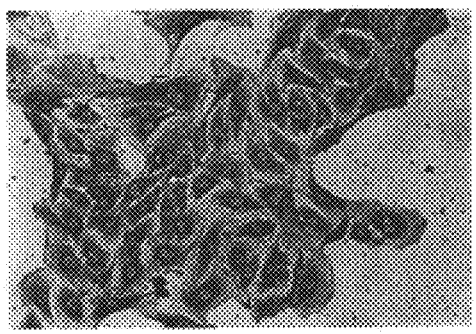

When cells were exposed to 1% sodium azide for 30 minutes prior to incubation with bR7, neither cytoplasmic nor nuclear staining was observed (FIG. 1E), indicating that the cellular uptake of arginine polymers is an energy dependent process. However, when the experiments were performed at 4° C., no apparent reduction was observed in the efficacy of bR7 translocation (FIG. 1D), which is incompatible with known endocytotic pathways. Nor was translocation of bR7 inhibited by the addition of free L-arginine up to 10 mM (FIG. 1F). High concentrations of extracellular L-arginine would be expected to compete for binding to the y+ transporter, which is known to transport monomers of basic amino acids (Deves 1998). Because exogenous L-arginine did not block the effect of the arginine polymers, the latter are not utilizing the transport system y+ to gain intracellular access. These results indicate that transport is not mediated by the basic amino acid transport system y+ or by classical endocytotic pathways.

Translocation of the polymers into endothelial cells (EC) was similarly examined, as described in Example 3. No internalized biotin signals were detected in control cultures treated with vehicle or with biotin alone, or in cells treated with biotin labeled heptalysine (bL-K7). However, even at the lowest concentration of b-R7 (0.1 $\mu$M), internalized biotin was observed in the cytoplasm of all EC. After treatment with 10.0 $\mu$M b-R7 for 30 minutes, internalized biotin was detected not only in the cytoplasm but also in the nucleus of virtually all exposed endothelial cells.

There were no observable differences in the distribution or intensity of internalized biotin between the L or D forms of heptaarginine (R7 and r7), indicating that polymer uptake is not significantly affected by the chirality of the arginine residues in the polymer under the conditions tested. These findings indicate that both L-R7 and D-r7 are very efficient at translocating across both cytoplasmic and nuclear membranes of VSMC and endothelial cells in culture, and act as a carrier for a second molecule, biotin.

B. Ex Vivo Translocation of Arginine Polymers

Figure 2A:
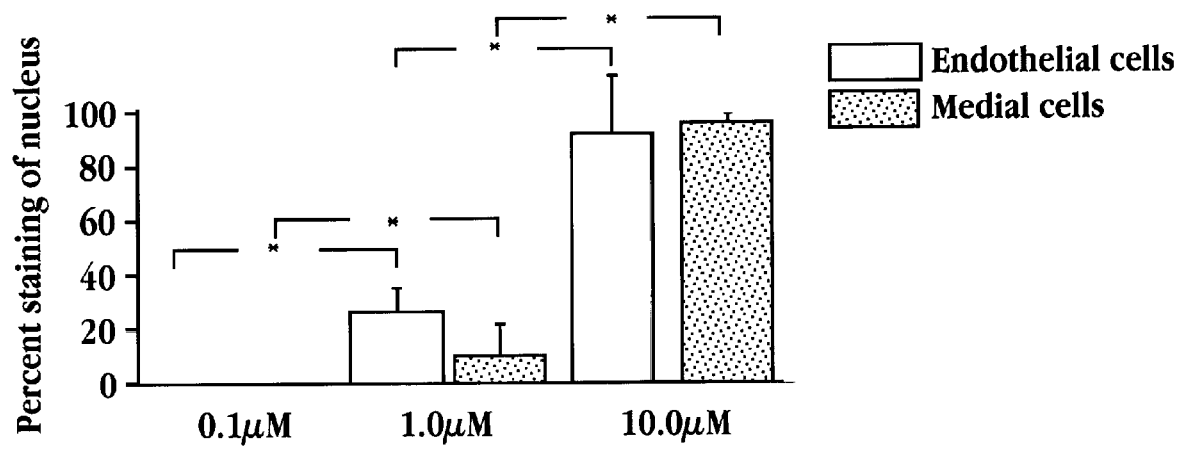
FIG. 2 shows dose, incubation time, and temperature dependence of R7 translocation in rabbit carotid artery segment. The magnitude of R7 translocation is expressed as percent stained nuclei (stained nuclei/total nuclei). (a) Dose dependence of bR7 translocation. (b–c) Time dependence of bR7 translocation at 4° C. and 37° C., in intimal cells and medial cells, respectively. Data are from 4 independent experiments. *, $p<0.05$.

Studies using rabbit carotid artery and jugular vein, as described in Example 4, were performed to evaluate the translocation ex vivo of the polymers. Microscopic examination of the treated carotid artery segments revealed a concentration-dependent uptake of biotin in both the cytoplasm and nucleus of all vascular cells. Following incubation for 30 minutes at a dose of 10.0 $\mu$M bL-R7, a distinct biotin signal was observed in virtually all intimal cells, medial cells, and adventitial cells. See FIG. 2A, where the magnitude of bL-R7 translocation is expressed as percent stained nuclei (stained nuclei/total nuclei). Jugular vein segments incubated with bL-R7 exhibited a similar staining pattern. When the carotid artery and jugular vein were incubated with biotnylated polylysine (bL-K7; 10 $\mu$M), no stained cells were apparent.

Figure 2B:
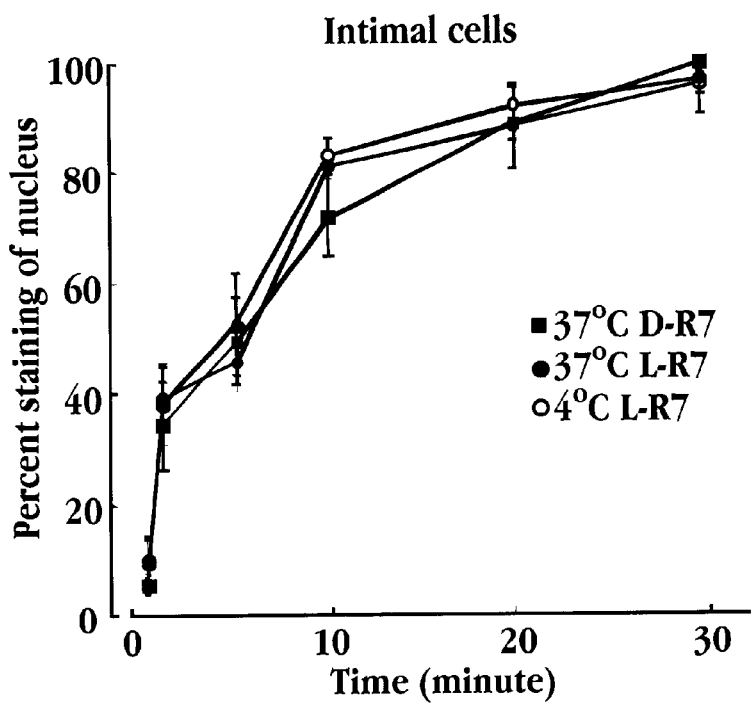
Figure 2C:
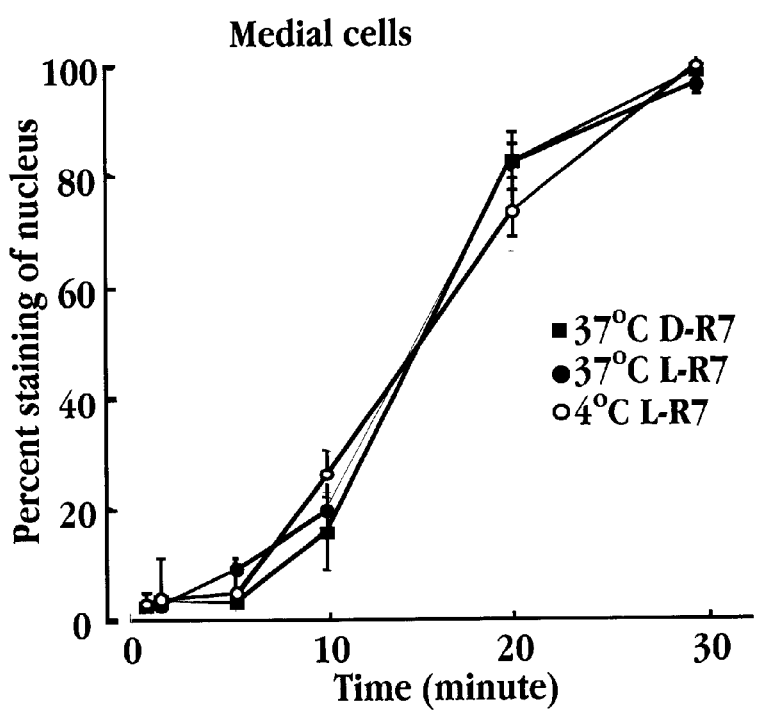

The extent and the intensity of staining of the polyarginine-treated tissues, as well as the depth of penetration within the tissue segment, increased in a time-dependent manner, so that within 30 minutes, virtually all vascular cells exhibited a distinct biotin signal in both the cytoplasm and nucleus (FIGS. 2B–C). These results are consistent with first-order kinetics for arginine polymer uptake.

When bR7 was instilled intraluminally, as described in Example 4, biotin signals were detected throughout the vessel, including the adventitial cells (outermost layer of the vessel), staining them intensely after 30 minutes of intraluminal exposure. There were no differences between D and L forms of heptaarginine in their ability to penetrate the vascular wall and translocate into all cells.

There was no apparent reduction in the speed or efficacy of bL-R7 translocation into vascular tissue when the experiments were performed at 4° C. (FIGS. 2B–C), indicating that R7 translocation was not dependent on classical endocytosis. Note that incubations of arginine polymer with vessel segments at lower temperatures (e.g., just above the freezing point) may be desired to preserve the vascular segments prior to grafting.

Figure 3A:
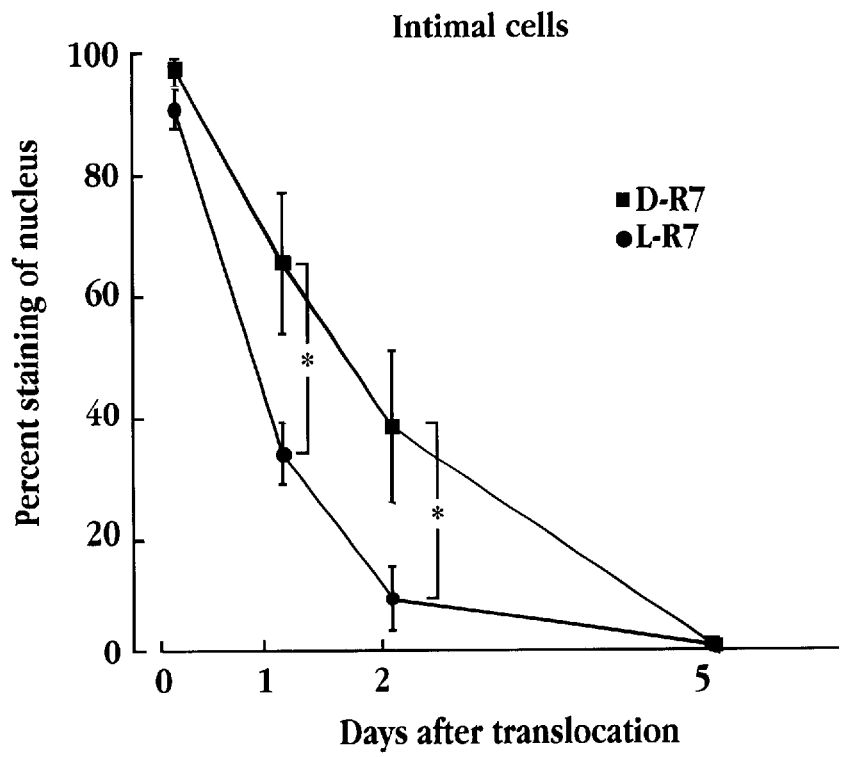
FIG. 3 shows the time course of disappearance of internalized biotin signal in bR7 treated artery segments; (a) intimal cells, (b) medial cells. Vascular segments exposed to biotin-labeled L-R7 or D-R7 (10.0 $\mu$M) were incubated in serum containing medium for up to 5 days. The magnitude of R7 translocation is expressed as percent stained nuclei. Data are from 4 independent experiments. *, $p<0.05$.
Figure 3B:
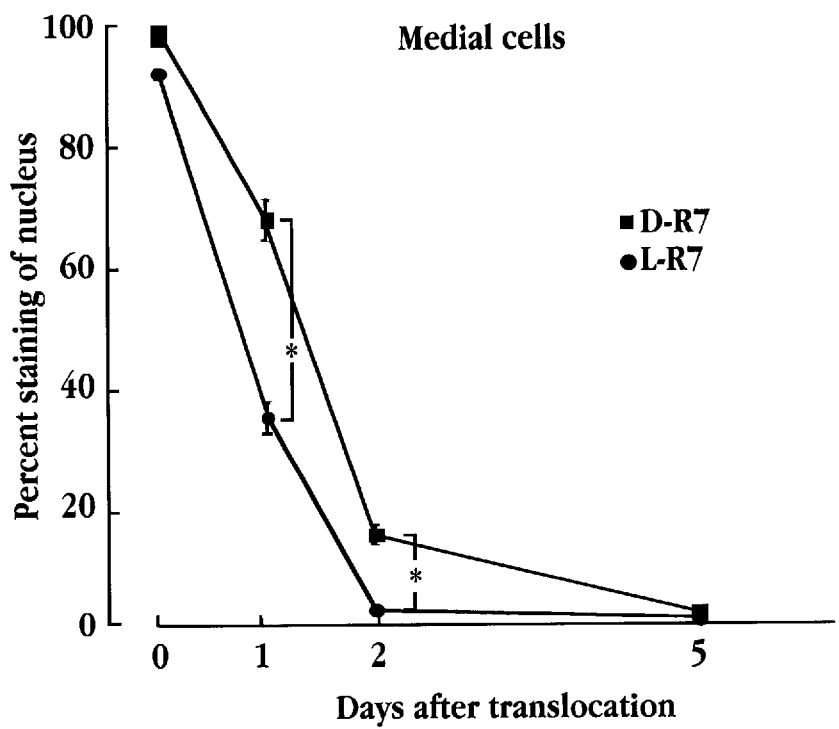

To estimate the relative stability of the D and L forms of heptaarginine in vivo, the disappearance of the biotin signal over time from vascular segments was observed by microscopic examination. At days 1 and 2 after exposure, residual nuclear biotin in both endothelial and medial cells was greater in vascular segments treated with bD-r7 than those treated with bL-R7 (FIGS. 3A–B). No significant positive staining was observed with either form by day 5, but it was not established whether this observation was the result of cellular degradation of the biotin moiety.

IV. Effect of Arginine Polymers on NO Production and Myointimal Hyperplasia

A. Enhancement of NO Production in Cytokine-Stimulated VSMC

Vascular nitric oxide (NO) is synthesized from L-arginine by endothelial cells, and contributes to vascular relaxation as well as maintenance of normal vascular structure (Lloyd 1996; Cooke 1997). It is well established that vascular NO inhibits monocyte adherence and chemotaxis (Tsao 1997), platelet adherence and aggregation (Radomski 1990; Wolf 1997), and vascular smooth muscle cell (VSMC) proliferation (Garg 1989).

Vascular endothelium normally expresses endothelial NO synthase (eNOS). In disease states, vascular cells also express inducible NO synthase (iNOS). Derangement of NO synthesis contributes to the development of vascular proliferative disorders, including atherosclerosis, restenosis after balloon angioplasty or other injury, and, vein graft disease (Lloyd 1996; Cooke 1997). Recent evidence suggests that preservation or enhancement of NO synthesis can prevent or reverse some of the pathophysiological processes that contribute to vascular proliferative diseases.

Because intracellular levels of L-arginine normally greatly exceed the $K_m$ of the NOS enzyme, NO synthesis is ordinarily not dependent on extracellular supplementation (Harrison 1997). However, under certain circumstances, local L-arginine concentration can become rate-limiting. Such circumstances include elevated plasma or tissue levels of the endogenous NO synthase antagonist ADMA (asymmetric dimethylarginine) (Boger 1998) and inflammation-induced expression of the inducible NO synthase (iNOS) (Guoyao 1998). Both of these abnormalities are operative in the setting of vascular injury (Dattilo 1997).

Inducible NOS is also stimulated, in a dose-dependent manner, by IFN-γ and LPS, as described in Example 5. Addition of extracellular L-arginine confirmed that L-arginine is a limiting factor for NO production in cytokine-stimulated VSMC. Both of these effects are shown in FIG. 4.

Figure 5:
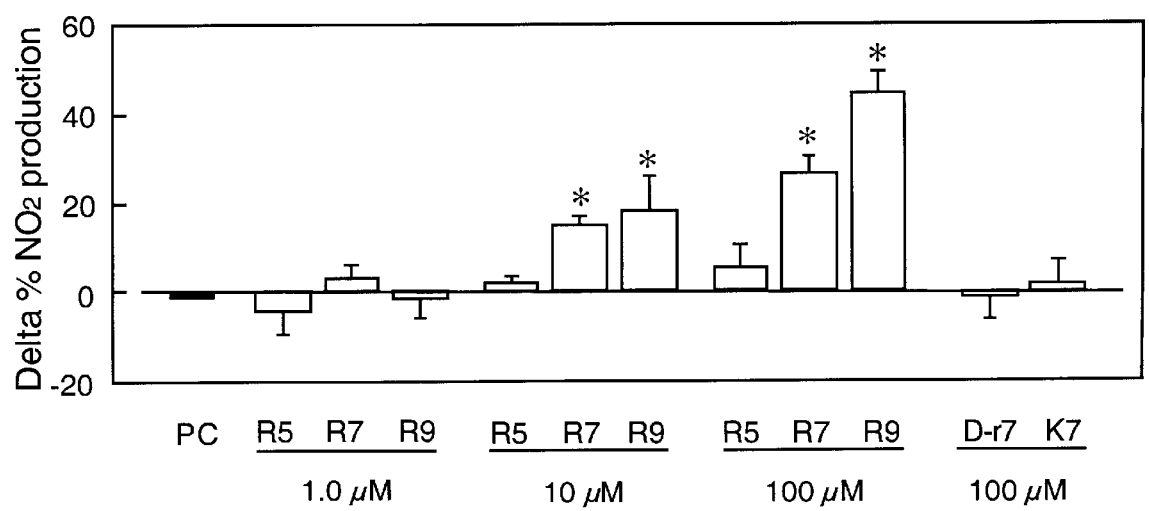
Figure 6:
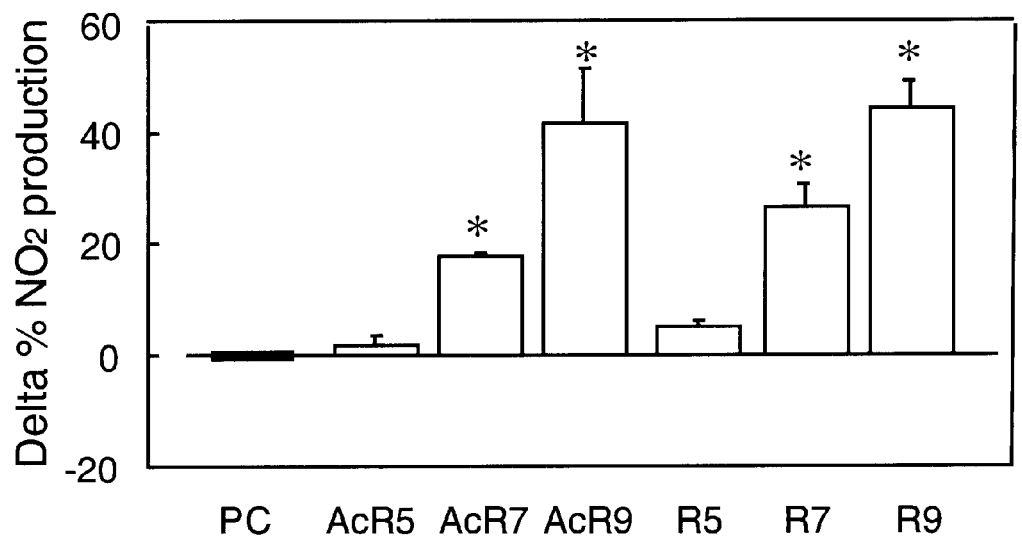
Figure 7:
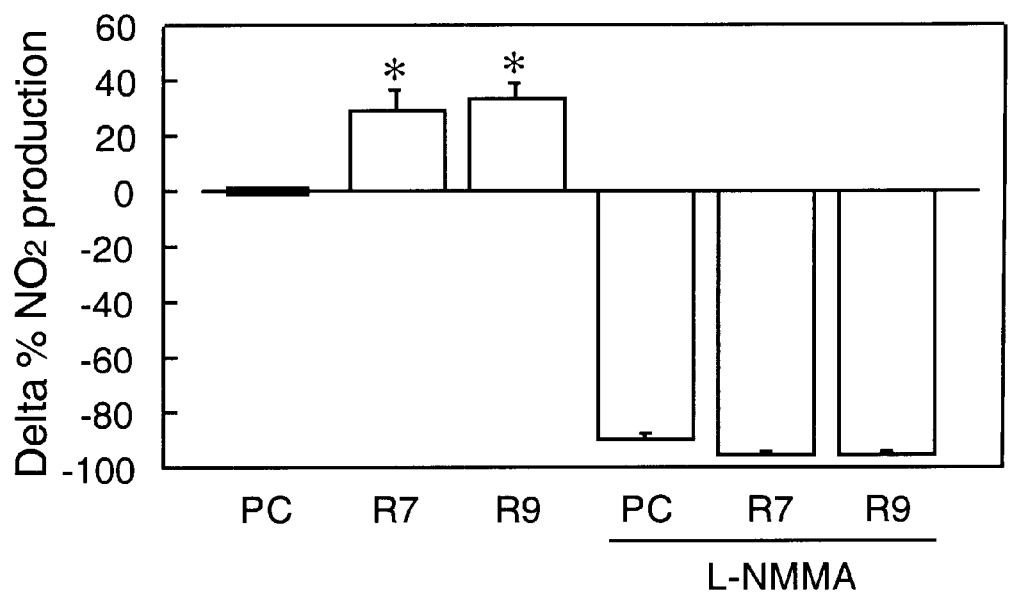

In accordance with the invention, poly(L)arginine oligomers enhance NO synthesis in vascular tissue. As described in Example 6, cytokine-stimulated VSMC incubated in physiological levels (100 μM) of extracellular (L)-arginine were treated with different length (L)-arginine oligomers, then stimulated with IFN-γ and LPS. Pretreatment with L-R5 for 30 minutes gave no significant enhancement of NO production. Pretreatment with L-R7 and L-R9, however, resulted in dose-dependent increases in NO production at doses as low as 10 μM (FIG. 5). The degree of enhancement was significantly greater in cells treated with R9 than those treated with R7 (24±3.8 vs. 44±5.2%, p<0:05). Treatment with D-r7 or K7 (polylysine) (100 μM, 30 minutes) did not increase the NO production (FIG. 5). N-terminal acetylation of the L-peptides (R5, R7 and R9), which delays intracellular degradation, had no significant effect on NO production after 24 hours (FIG. 6). When R7 treated cells were subsequently treated with the NO synthase inhibitor, L-NMMA, the enhancement of NO production was abolished (FIG. 7).

The arginine oligomers were found to be significantly more efficacious, on a mass basis, than equivalent amounts of free arginine monomer, which is not significantly taken up by the walls of arterial and venous segments. When VSMCs were exposed to R7 for 5 minutes, a sustained increase in NO biosynthesis was observed for 24 hours. By contrast, exposure of VSMCs to high levels (1 mM) of free L-arginine for 5 minutes did not significantly increase NO biosynthesis (data not shown).

It is proposed that the (L)-arginine oligomers enhance NO production by supplementing intracellular (L)-arginine levels. In order to clarify whether R7 translocation affects iNOS protein expression in cytokine-stimulated VSMC, iNOS protein expression was examined by western blotting (Example 7). Inert rat VSMC did not express detectable iNOS protein (130 KDa). When the cells were stimulated by IFN-γ and LPS, demonstrable expression of iNOS protein was observed, as expected. Treatment with R7 (10 μM, 30 minutes exposure), however, had no effect on the expression levels of iNOS. Therefore, the enhancement of NO production by the L-arginine oligomers, R7 and R9, was not due to an increase in iNOS expression.

As demonstrated above, arginine polymers of the invention are extremely efficient at translocating into vascular cells. The cellular translocation is energy dependent, but does not involve classical endocytosis, nor the basic amino acid transporter. Pretreatment of cells with R7 (10 μM) caused a significant elevation of NO production which was not observed when cells were treated with high concentrations of free L-arginine (up to 1 mM). These findings indicate that cellular uptake of the short polymers of arginine is uniquely efficient, with different kinetics than the y+ transport system.

B. Effects of D- and L-Arginine Polymers on NO Production and on Myointima Formation in Vein Grafts Myointimal hyperplasia involves the migration and proliferation of VSMCs in the intima, accompanied by elaboration of extracellular matrix (DeMeyer 1997). Within 24 hours of a vascular injury (e.g. interposition of a vein graft or balloon angioplasty), VSMC express iNOS (Morris 1994; Hansson 1994). Vascular NO, derived largely from iNOS in the setting of vascular injury, may play an important role in suppressing VSMC hyperplasia (Lloyd 1996; Cooke 1997), by inhibiting monocyte adherence and infiltration and VSMC proliferation and by inducing VSMC apoptosis (Tsao 1996, 1997; Garg 1989).

In view of the extremely efficient transport of arginine oligomers into vascular cells, as demonstrated above, and the enhancement of intracellular NO levels by poly(L) arginine, the ability of these polymers to inhibit intimal hyperplasia was investigated. Vein grafts were carried out on male New Zealand white rabbits, as described in Example 8. After excision and prior to grafting, the jugular vein was gently flushed and immersed in PBS (control) or in PBS containing either L-R7 or D-r7 (10.0 μM) for 30 minutes. L-R5 and D-r5 (10.0 μM), which have been previously demonstrated not to translocate across the cell membrane, were also used as controls.

Figures 8A, 8B, 8C:
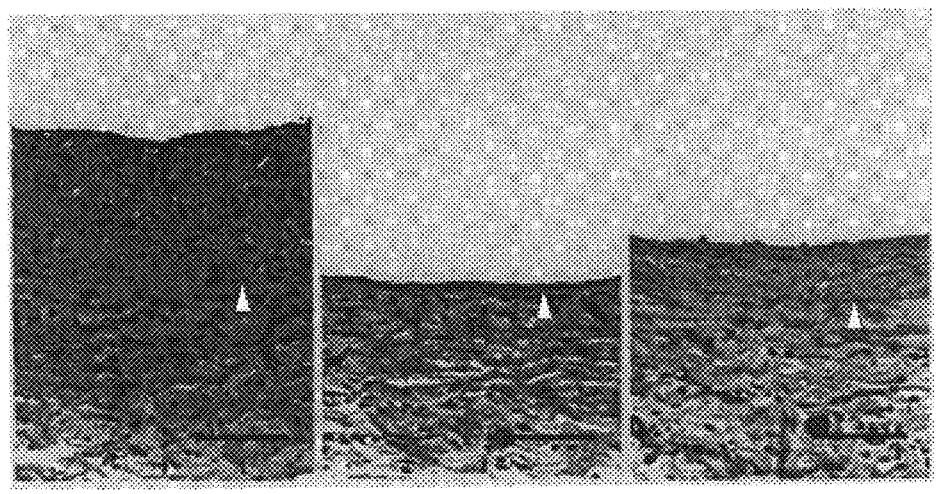
FIG. 8 shows representative photomicrographs of cross sections of (a) vehicle treated, (b) L-R7 treated (10.0 μM), and (c) D-R7 treated (10.0 μM) vein grafts harvested on the 28th day postsurgery. Arrowheads indicate the internal elastic lamina. (Hematoxylin Eosin staining, X100, bars=100 μm).
Figure 9A:
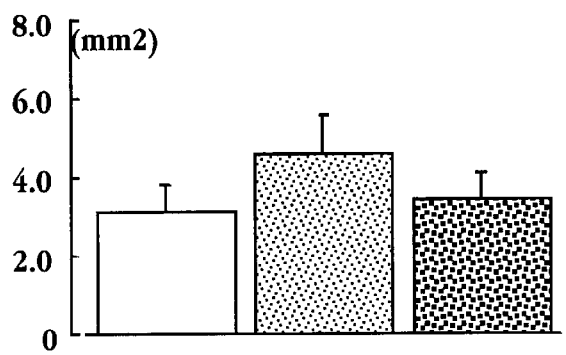
FIG. 9 shows planimetric measurements of vein graft segments harvested on the 28th day after surgery. (a) luminal area; (b) medial area; (c) intimal area; (d) I/M ratio. I/M represents the ratio of intima to media area. Each experimental group was composed of 6 animals *, $p<0.05$.
Figure 9B:
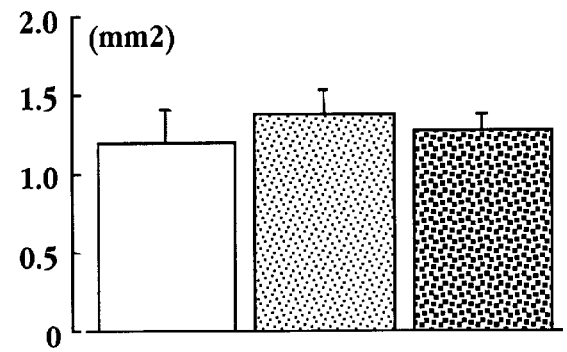
Figure 9C:
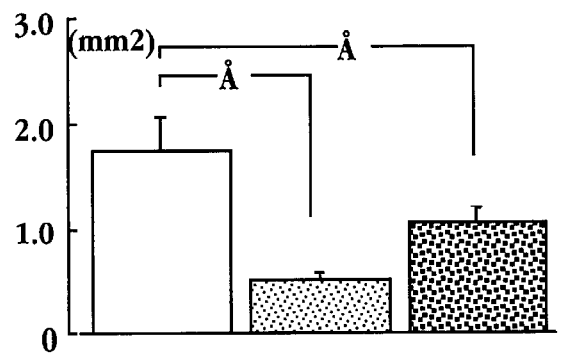
Figure 9D:
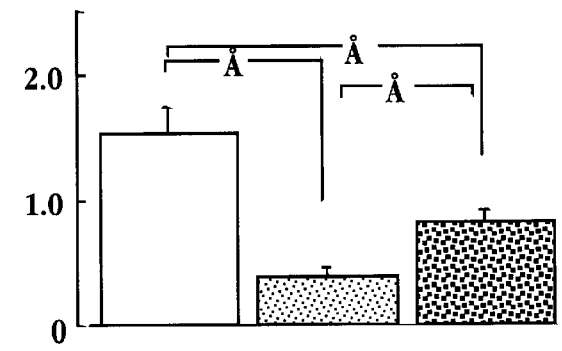

All vein grafts treated with vehicle alone developed significant myointimal hyperplasia 28 days after surgery (FIG. 8A; arrowheads indicate internal elastic lamina). By contrast, vessel segments treated with either L-R7 (FIG. 8B) or D-r7 (FIG. 8C) had substantially less myointima formation (intimal area: control; 1.7±0.8, L-R7; 0.5±0.2, D-r7; 1.1±0.4 mm², p<0.05). Treatment with L-R7 was more effective than D-r7, reducing intimal area by more than 70%, vs. about 35% for D-r7. The intima/media ratio (I/M) of L-R7-treated vein grafts was also significantly less than both control and D-r7-treated grafts (I/M: Control; 1.5±0.5, L-R7; 0.4±0.2, D-R7; 0.8±0.2, p<0.05). Treatment using the smaller oligopeptide (R5), which translocates poorly across membranes, was not effective in inhibiting myointima formation, suggesting that the observed inhibitory effects were due to translocation of the heptamers of arginine and not simply the availability of polyarginine, e.g. complexed to the cell membrane.

The greater activity of the L-polymer is consistent with proteolysis to form L-arginine monomers, which can promote formation of NO. Thus, it will be appreciated how the composition of the arginine polymer can be modified to achieve variations in the rate of arginine release. The rate of arginine release may be attenuated by including one or more D-arginine residues, which slow the rate of proteolytic breakdown of the polymer. In addition, D-Arg must be converted to L-Arg (see below) before it can serve as a substrate for NO synthase. In one embodiment, all of the arginine residues in the polymer have an L-configuration, for more rapid biological activity.

Figure 10A:
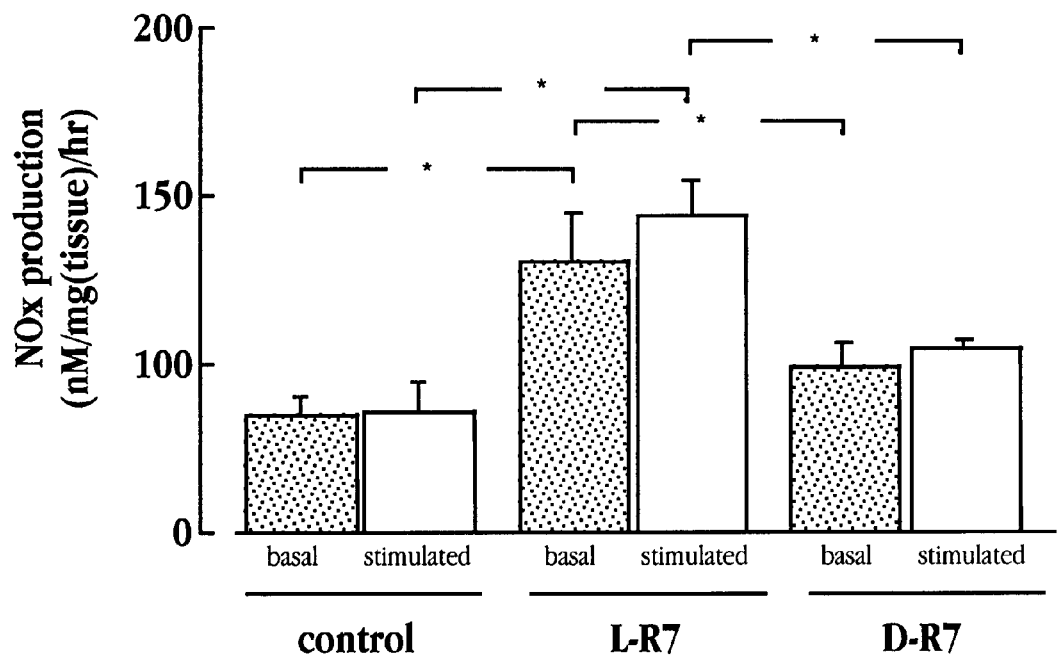
FIG. 10a shows $NO_x$ (nitrate and nitrite) production measured from vein graft segments harvested 3 days after surgery. Graft segments were incubated in medium in either the absence (basal) or presence (stimulated) of calcium ionophore. Each experimental group is composed of 3 vessel segments. *, $p<0.05$.

Grafts were harvested after 3 days for assessment of NO production, as described in Example 9. Basal $NO_x$ production from L-R7 treated vein grafts was significantly higher than that of both control and D-r7 treated vein grafts, as shown in FIG. 10A (control; 35±6, L-R7; 80±14, D-r7; 48±8 nM/mg tissue/hr, p<0.05). There was no significant difference in basal $NO_x$ production between D-r7-treated and vehicle-treated vein grafts.

Calcium ionophore stimulation of eNOS did not significantly affect the $NO_x$ production by the vein grafts (FIG. 10A). Graft segments were incubated in medium in either the absence (basal) or presence (stimulated) of calcium ionophore. This finding suggests that the majority of NO was generated by the calcium-independent inducible form of NO synthase (rather than the endothelial isoform), and is compatible with previous reports of iNOS expression in VSMC after vein grafting.

Because D-arginine is not a substrate for NO synthase, its inhibitory effect on myointimal hyperplasia was surprising. The effect of D-r7 could be due to NO production after epimerization of D- to L-arginine (Wang et al., 1999; D'Aniello et al., 1993). It is also known that D-arginine may be oxidized to D-citrulline and NO by a non-enzymatic reaction involving hydrogen peroxide (Nagase et al., 1997).

Alternatively, there may be NO-independent mechanism(s) of polyarginine action. Both L-R7 and D-r7 treatment inhibited proliferation of VSMC in vitro. Because nonstimulated VSMC express neither constitutive nor inducible NO synthase, this inhibitory effect seems to be NO-independent. One possible NO-independent effect of the arginine polymers might be mediated by a cationic interaction with nucleic acid; arginine rich sequences are often found in RNA-binding proteins.

Figure 10B:
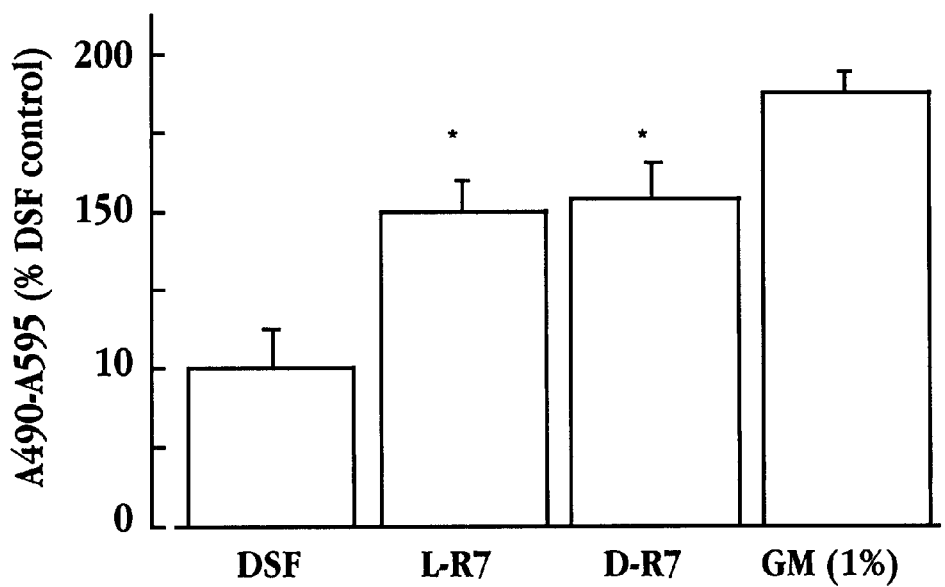
FIG. 10b shows NO-independent effects of heptaarginines on cell proliferation. Rat VSMC were incubated with either L-R7 or D-r7 (10.0 μM, 30 minutes), then incubated with growth medium containing 0.5% FBS for 48 hours. Cell proliferation was measured using XTT assay; percent OD of each treatment group to group treated with serum free medium (DSF) was calculated. Data are from 6 experiments. *, $p<0.05$ vs. growth medium (GM) control group.

Direct cytostatic properties of arginine oligomers were investigated, as described in Example 10. Rat VSMC were incubated with either L-R7 or D-r7 (10.0 μM, 30 minutes), then incubated with growth medium containing 0.5% FBS for 48 hours. Cell proliferation assays revealed that, in the absence of NOS enzyme, VSMC proliferation was significantly inhibited by pretreatment with either L-R7 or D-r7, as compared to vehicle incubation. There were no significant differences between L-R7 and D-r7 treatment groups in this NO-independent cytostatic effect (FIG. 10B).

C. Effects of L-Arginine Polymers on GCAD in Heart Transplant Model

Graft coronary artery disease (GCAD) is characterized by diffuse neointimal hyperplasia in the coronary arteries of the transplanted heart. As discussed above, nitric oxide (NO) limits the development of neointima formation by inhibiting vascular smooth muscle cell proliferation.

In this study, PVG rat donor hearts (n=48) were transplanted heterotopically into the abdomen of ACI recipients. Donor hearts received either intracoronary PBS or intracoronary 50 uM (L)-arginine polymer (L-R5 or L-R9) for 30 minutes. (D-arginine polymers were not included in this study.) Each of these groups was further divided into 60 and 90 day study animals (n=6 each). Percent luminal narrowing, intima to media ratio (I/M), and percent affected vessels were determined as described in Example 11, below. Transfection efficiency was determined by infusing biotinylated R5 and R9, as in the preceding studies, and calculating the percentage of biotin positive nuclei divided by total number of nuclei.

Results are shown in Table 1, below. As the data show, the R5 oligomer demonstrated minimal transfection of coronary vessels and essentially no difference in GCAD compared to PBS controls at both 60 and 90 days. The R9 groups, however, demonstrated both marked transfection of the intima and media of coronary vessels and a significant reduction in GCAD (p values<0.05) at post op days 60 and 90.

TABLE 1

Transplant Study

| Treatment | % luminal narrowing | I/M ratio | % affected vessels |
|---|---|---|---|
| PBS - 60 days | 11.3 ± 4.2 | .12 ± .05 | 22.9 ± 9.5 |
| PBS - 90 days | 18.5 ± 13.7 | .13 ± .08 | 22.9 ± 15.7 |
| R5 - 60 days | 12.6 ± 6.7 | .13 ± .07 | 18.9 ± 7 |
| R5 - 90 days | 14.2 ± 12 | .16 ± .14 | 18.5 ± 11.9 |
| R9 - 60 days | 3.2 ± 3.8 | .03 ± .04 | 6.5 ± 6.9 |
| R9 - 90 days | 1.6 ± 3.3 | .01 ± .02 | 4.9 ± 7.1 |

V. Isolated Vessel Conduit

In a further embodiment, the invention provides an isolated vascular vessel conduit, such as an arterial segment, venous segment, or an artificial vessel segment, which is prepared to contain a polymer of arginine as described herein. Any suitable conduit can be used. As used herein, "isolated" refers to a conduit that, prior to grafting, exists outside of the subject's body. Exemplary arterial conduits include segments of internal mammary artery (IMA), internal thoracic artery, and gastroepiploic artery. Venous segments can be prepared from various sources, preferably from a cutaneous vein from a subject's arm or leg, such as a saphenous vein. Preferably, the vessel segment is an autologous saphenous vein or an internal mammary artery segment. However, venous and arterial segments from other human donors (allografts) can also be used, as well as vessel segments obtained from other animals (xenografts), such as pigs. Conveniently, the segment is obtained from the subject who is to receive the vessel conduit graft. In addition, the vessel conduit can also be provided as an artificial vessel segment made from a physiologically compatible material, such as "DACRON"™, PTFE, or other non-tissue graft materials, and which preferably is prepared or derivatized, e.g., by carboxylation, sulfonation, or phosphorylation, to contain negatively charged groups for adsorbing the positively charged arginine polymer. The artificial vessel segment can also be partially porous in its internal wall to provide a reservoir region from which the arginine polymer can gradually diffuse after the conduit has been grafted into the subject. Although intimal hyperplasia would not occur within artificial segments, it can be especially problematic at the anastomotic junctions where the terminal ends of the artificial segment join to the subject's vascular system. Thus, such intimal hyperplasia adjacent to the grafted vessel conduit can be inhibited by the arginine polymer.

For grafting, the vessel conduit may be of any suitable length, e.g., 3 to 12 inches in length. Multiple vessel segments from the same subject may be used, including both arterial and venous segments.

The arginine polymer is preferably dissolved in a sterile, physiologically suitable liquid that minimizes disruption of the physical and biological function of the vessel conduit. Exemplary liquids include serum-free culture media, such as serum-free Dulbecco's minimal essential medium (DMEM), aqueous solutions such as 0.9% (w/v) saline (NaCl), and any other sterile liquid medium or solution that is used in vessel grafting procedures. The polymer is provided at a concentration that achieves the desired effect. Typically, the polymer concentration is from 0.01 $\mu$M to 100 $\mu$M, preferably 1 $\mu$M to 50 $\mu$M, or 1 $\mu$M to 25 $\mu$M, although concentrations above or below these ranges may also be used.

The vessel conduit is contacted with the arginine polymer-containing liquid for a time sufficient for the arginine polymer to be taken up into the wall of the vessel, so that a reduction in intimal hyperplasia is obtained after graft. For example, the vessel conduit can be immersed in the solution so that the arginine polymer penetrates both the interior and exterior walls of the vessel. Alternatively, the polymer solution can be placed inside the vessel with both ends closed by ligation, clamping, or the like, so that only the intraluminal wall is exposed to the polymer. Usually, the polymer liquid is contacted with the vessel segment for from 60 seconds to 120 minutes, more typically between 5 and 45 minutes, and preferably for a time that is less than 30 minutes. Generally, less contact time is necessary with higher concentrations of arginine polymer. The contacting step can be performed at any appropriate temperature, typically at a temperature from 4° C. to 37° C., and conveniently at ambient room temperature.

Before or after the vessel conduit is contacted with the arginine polymer solution, the vessel segment may be stored in the same types of liquids mentioned above, without the arginine polymer. Preferably, the venous and arterial vessel segments are maintained ex vivo for as brief a time as possible, to help avoid degradation of their function.

The site where the vessel conduit is to be grafted can be prepared by conventional methods, e.g., for a coronary bypass or an above-knee or below-knee femoro-popliteal arterial bypass procedure. Damaged or necrotic tissue is removed, and the site is surgically prepared for attachment of the new vessel conduit, preferably during the time that the vessel conduit is being contacted with the arginine polymer. Following the graft procedure, the subject may be monitored periodically to verify physiological acceptance of the graft and to assess the level of blood flow through the grafted vessel over time.

VI. Treatment Methods

As shown above, the polymers of the invention are useful in reducing post-graft and post-transplant hyperplasia. Accordingly, the invention provides a method in which one or both of the vascular vessel regions adjacent to an incoming vessel conduit are contacted with a solution of an arginine polymer as described herein, to inhibit post-graft intimal hyperplasia in these regions. For example, after a necrotic vessel segment (lesion) has been removed (transected), the remaining vascular region downstream from the excision site (distal to the heart) is clamped at a point several centimeters (e.g., 4 cm) from the proximal end of the downstream (distal) region, the clamped region is filled with arginine polymer solution, and the proximal end is then clamped to create a "sausage" containing the polymer solution. After the arginine polymer solution has been incubated in the clamped region for an appropriate time, the proximal clamp is removed, and the arginine polymer solution is optionally removed, followed by removal of the remaining clamp.

A similar procedure can be performed on the vascular region upstream of the excision site where the vessel conduit is to be grafted. By contacting the inner walls of the distal and proximal vascular regions in the subject adjacent to the graft site, before the vessel conduit is grafted into the subject, the zone of protection against intimal hyperplasia can be extended around the graft site, thereby increasing the probability of success. This method is particularly useful for artificial vessel grafts, to inhibit intimal hyperplasia at the anastomotic junctions.

Inhibition of intimal hyperplasia in a vessel extends to the use of the polymers of the invention to treat "patches" of arterial walls, e.g. vein patches used to repair arteries which have undergone endarterectomy for atherosclerotic plaques. Such patches, when untreated, often undergo intimal hyperplasia.

Another application in which the invention finds use is in the vascular access model of kidney dialysis, where a surgically formed arterial-venous anastomosis or shunt provides access to the artery and vein used for dialysis. During dialysis, the rate of blood flow, turbulence and stress at the venous junction is much higher than in a normal vein. Repeated exposure to these pressures frequently leads to hyperplasia and stenosis within the vein, causing dialysis access failure (see, for example, reviews by Himmelfarb, 1999 and Woods et al., 1997). Under these circumstances, repeated surgeries must be performed on fresh vessel segments. In accordance with the present method, in the anastomosis procedure, the vein segment to be grafted is exposed to an arginine polymer solution, typically by infusion into the clamped segment, prior to attachment to the target artery. This treatment significantly reduces hyperplasia and extends the useful lifetime of the anastorriosis, thus reducing the need for further surgery.

The method and compositions of the invention may also be used in prevention of vasculopathy, or chronic rejection of transplanted organs. Prevention of GCAD in a heart transplant model is demonstrated above. Preferably, the organ, such as a heart or kidney, is retrieved from the donor into an arginine polymer solution. Currently used preservation/transport media, such as Cardioplegin™, could be supplemented with the polymer. The polymer is provided at a concentration that achieves the desired effect. Typically, the polymer concentration is from 0.01 $\mu$M to 100 $\mu$M, preferably 1 $\mu$M to 50 $\mu$M, or 1 $\mu$M to 25 $\mu$M, although concentrations above or below these ranges may also be used. The organ to be transplanted is contacted with the arginine polymer-containing liquid for a time sufficient for the arginine polymer to be taken up into the vascular tissues of the organ, so that a reduction in intimal hyperplasia is obtained after transplant.

The grafting method of the invention also contemplates use in conjunction with any other ameliorative procedures which may facilitate the success of the graft. For example, the subject can be placed on an arginine-rich diet to increase vascular NO levels, as taught in U.S. Pat. Nos. 5,428,070, 5,852,058, 5,861,168, and 5,891,459 by J. P. Cooke and coworkers, which are incorporated herein by reference. In addition, anti-thrombotic drugs such as heparin may be administered shortly before and after grafting to help reduce the possibility of thrombus formation.

VII. Formulations

Compositions and methods of the present invention have utility in the area of human and veterinary vascular therapeutics. The intrinsic biological effects of the subject oligomers, in enhancing NO synthesis and/or inhibiting intimal hyperplasia, are useful in preventing or treating vascular disease or injury, particularly in treating vascular proliferative disorders such as post-operative restenosis. In addition, the polymers are useful in the area of intracellular delivery of therapeutic agents which show limited cell entry in unconjugated form.

Stability of the oligomers can be controlled by the composition and stereochemistry of the backbone and sidechains. For polypeptides, D-isomers are generally resistant to endogenous proteases, and therefore have longer half-lives in serum and within cells. For use of the subject oligomers in inhibition of intimal hyperplasia, oligomers which generate L-arginine in vivo, e.g. L-arginine oligomers, are preferred. As shown above, however, D-arginine oligomers, which are not readily degraded to arginine, were also effective in this area.

The compositions typically include a conventional pharmaceutical carrier or excipient and may additionally include other medicinal agents, carriers, adjuvants, and the like. Preferably, the composition will be about 5% to 75% by weight of a compound or compounds of the invention. As noted above, media used for heart transplants may include a cardioplegic agent such as Cardioplegin™, a mixture of magnesium aspartate, procaine, and sorbitol, or similar compositions (see e.g. Isselhard et al., 1980). Appropriate excipients can be tailored to the particular composition and route of administration by methods well known in the art.

Liquid compositions can be prepared by dissolving or dispersing the polymer (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a suspension or, preferably, a solution. As discussed above, the polymer solution can be used to immerse a vessel or organ to be grafted or transplanted, prior to surgery.

The polymers may also be delivered to a vessel post-surgically or following an angioplasty procedure. Devices for delivery of a medicament to the lumen of a vessel are known in the art and include, for example, perforated or porous catheter balloons containing the medicament. Such a delivery device may also incorporate a biocompatible polymeric carrier, such as a Pluronic™ hydrogel, containing the medicament.

The compounds of the invention are administered in a therapeutically effective amount, i.e., a dosage sufficient to effect treatnent, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

Administered dosages will generally be effective to deliver picomolar to micromolar concentrations of the therapeutic composition to the site. Appropriate dosages and concentrations will depend on factors such as the therapeutic composition or drug, the site of intended delivery, and the route of administration, all of which can be derived empirically according to methods well known in the art.

For certain applications, e.g. delivery to a site of angioplasty, the surface area of tissue to be treated may also be considered. For delivery to the site of vessel injury, in vivo models such as described in Edelman, 1995, may be used. Further guidance can be obtained from studies using experimental animal models for evaluating dosage, as are known in the art.

Methods for preparing such dosage forms are known or will be apparent to those skilled in the art; for example, see *Remington's Pharmaceutical Sciences* (19th Ed., Williams &,Wilkins, 1995). The composition to be administered will, in any event, contain a quantity of the active compound(s) in a pharmaceutically effective amount for relief of the condition being treated when administered in accordance with the teachings of this invention. Compositions for use in the methods described herein may also be enclosed in kits and/or packaged with instructions for use.

EXAMPLES

The following examples are intended to illustrate but not limit the present invention.

Materials and Methods

Cell Culture

Rat VSMCs were prepared from the media layer of thoracic aorta of Sprague-Dawley rats by the explant method. The cells were cultured in Dulbecco's modified Eagle's medium (DMEM, Gibco BRL, Gaithersburg, Md.) containing 10% fetal calf serum, 100 U/ml penicillin and 100 $\mu$g/ml streptomycin at 37° C. under a humidified atmosphere containing 5% $CO_2$. After subconfluent growth, cells were cultured with MEM Select Amine Kit (Gibco BRL, Gaithersburg, Md.) to be treated by specific concentrations of extracellular free L-arginine. Experiments were performed using cultured cells at passage levels of 5–10.

Histological Detection of Internalized Biotin Labeled Oligomers

After incubation with biotin labeled oligomer, vascular segments were washed, then frozen in OCT compound (Miles Scientific). Frozen sections, 5 $\mu$m thick, were fixed with acetone for 10 minutes. Internalized biotin was detected using the staining procedure described in Example 2. Methyl green was used for nuclear counter staining.

To quantify the efficiency of nuclear translocation, the numbers of both DAB positive nuclei and total nuclei were counted in the intima and media separately at ×400 magnification with a video image analysis system (Automatrix). The frequency of nuclear translocation was expressed as the percent staining of nuclei, defined as the ratio of the number of DAB positive nuclei to that of all nuclei, in the intima and media. Each protocol was repeated 4 times.

$NO_2$ Measurement

Extracellular NO production was measured as its stable oxidative metabolite, nitrite ($NO_2$). At the end of each incubation, samples of the medium (80 µl) were collected, and $NO_2$ measurement was performed using the Griess reaction facilitated by a commercial calorimetric assay (Cayman Chemical, Ann Arbor, Mich.). Values of $NO_2$ production were corrected with relative cell count assessed by a cell proliferation kit II (XTT) (Boeheringer Mannheim, Germany).

Statistical Analysis

All values are expressed as mean±SEM. Means were compared using an analysis of variance, and p values less than 0.05 were accepted as statistically significant.

Recombinant rat recombinant interferon-γ, *e.coli* lipopolysaccharide (0111:B4), and L-NMMA ($N^G$-monomethyl L-arginine) were purchased from Sigma Chemical (St. Louis, Mo.). A monoclonal anti-iNOS antibody was purchased from Transduction Laboratories (Lexington, Ky.), and gout anti-mouse IgG antibody conjugated with horseradish peroxidase was obtained from Kirkegaard and Perry Laboratories (Gaithersburg, Md.).

Experimental protocols were approved by the Administrative Panel on Laboratory Animal Care of Stanford University, and were performed in accordance with the "Guide for the Care and Use of Laboratory Animals" issued by National Institute of Health (NIH Publication No. 80-23, revised 1985).

Example 1

Peptide Synthesis

Peptides were synthesized using solid-phase techniques and commercially available Fmoc amino acids, resins, and reagents (PE Biosystems, Foster City, Calif., and Bachem, Torrence, Calif.) on a Applied Biosystems 433 peptide synthesizer as previously described (Hill 1994).

Example 2

Translocation of Biotin-Labeled Peptides into VSMC

Rat VSMCs were grown on glass microscope slide chambers (Nunc Inc., Naperville, Ill.). Subconfluent cells were washed and placed in serum-free medium. After 2 hours, cells were treated with bR7, or bK7 (0.1 µM, 1.0 µM, 10 µM), at 37° C. for 30 minutes. To assess the role of endocytosis in cellular uptake of the peptides, experiments were performed at 4° C., and also in the presence of sodium azide (1.0%) for 30 minutes prior to exposure to the peptides. To assess the involvement of the basic amino acid transport system y+ in the translocation of peptides into the cell, experiments were performed in the presence of excess extracellular L-arginine (10 mM).

After 30 minutes of incubation with the peptides, cells were washed 3 times with phosphate-buffered saline (PBS), fixed for 5 minutes at −20° C. in ethanol/acetone, washed 3 times in PBS, incubated for 30 minutes with a peroxidase suppressor (ImmunoPure, Pierce, Rockford, Ill.) to block endogenous peroxidase activity and nonspecific binding, washed, and then incubated with 5 µg/ml of horseradish peroxidase (HRP) conjugated strepavidin (Pierce, Rockford, Ill.) for 30 minutes. Cells were washed 3 times with PBS, and a substrate of HRP, DAB (Sigma, St. Louis, Ill.), was added to the cells. The reaction was terminated by washing in distilled water after a 60-second incubation with DAB. Cell preparations were observed by conventional light microscopy (see FIG. 1). This experimental protocol was repeated 3 times.

Example 3

In Vitro Translocation Study

Spontaneously transformed human umbilical vein endothelial cells (ECV304, ATCC) were cultured in medium M199 (Irvine Scientific) containing 10% fetal bovine serum (FBS), 100 IU/ml penicillin and 100 µg/ml of streptomycin (Gibco BRL). Confluent cells were washed and placed in serum-free medium. After 2 hours, the cells were incubated in presence of biotin labeled peptides, as bL-R7, or bD-R7, or bL-K7 (0.1, 1.0, and 10.0 µM). After 30 minutes of incubation, cells were washed 3 times with phosphate-buffered saline (PBS), fixed in ethanol/acetone; washed in PBS; incubated for 30 minutes with peroxidase suppressor (ImmunoPure, Pierce) to block endogenous peroxidase activity; and then incubated with 5 µg/ml of horse-radish peroxidase (HRP) conjugated strepavidin (Pierce) for 30 minutes. Substrate of HRP, diaminobenzidine (DAB, Sigma), was added to the cells. The reaction was terminated by washing in distilled water after a 60-second incubation. This experiment was repeated 3 times.

Example 4

Ex Vivo Translocation Study

Both carotid artery and jugular vein segments of male New Zealand white rabbits were used. To test the dose dependence of R7 translocation, vascular segments were incubated for 30 minutes with either bL-R7 or bD-R7 solution (0.1, 1.0, and 10.0 µM) in serum-free Dulbecco's minimal essential medium (DMEM) (Gibco BRL). To test the incubation time dependence, vascular segments were incubated with 10.0 µM of biotin labeled R7 solution for 10 seconds, 60 seconds, 5 minutes, 10 minutes, and 30 minutes. Furthermore, to determine the ability of R7 to penetrate through the vessel wall, vascular segments were ligated one end, R7 containing medium was instilled, and the other end ligated so as to expose only the luminal surface to R7. The luminal surface of the vascular segment was exposed to bL-R7 or bD-R7 (10.0 µM) for 30 minutes. To test the temperature dependence of translocation, vascular segments were incubated with 10.0 µM of biotin labeled R7 solutions at 37° C. or 4° C. To determine the disappearance time course of translocated R7, vascular segments were incubated with biotin labeled R7 solutions (10.0 µM) at 37° C. for 30 minutes, and then reincubated in DMEM with 10% FBS up to 5 days. Vascular segments were harvested at 1, 2 and 5 days after initial incubation.

Example 5

Stimulation of Cells with Interferon-γ and LPS

Cells were plated at a density of $5 \times 10^3$ per well into 96-well plates. For experiments assessing the effect of extracellular L-arginine concentration on NO synthesis from cytokine stimulated VSMC, subconfluent cells were washed twice with arginine free medium, then incubated for 24 hours with the medium containing the desired concentration of L-arginine (0, 10 μM, 100 μM, 1 mM, 10 mM). After 24 hours of incubation, the cells were then treated with a mixture of IFN-γ (100 U/ml) and LPS (100 μg/ml) in the medium containing the same dose of L-arginine for another 24 hours, and nitrite ($NO_2$) accumulation in the culture medium was quantified.

Figure 4A:
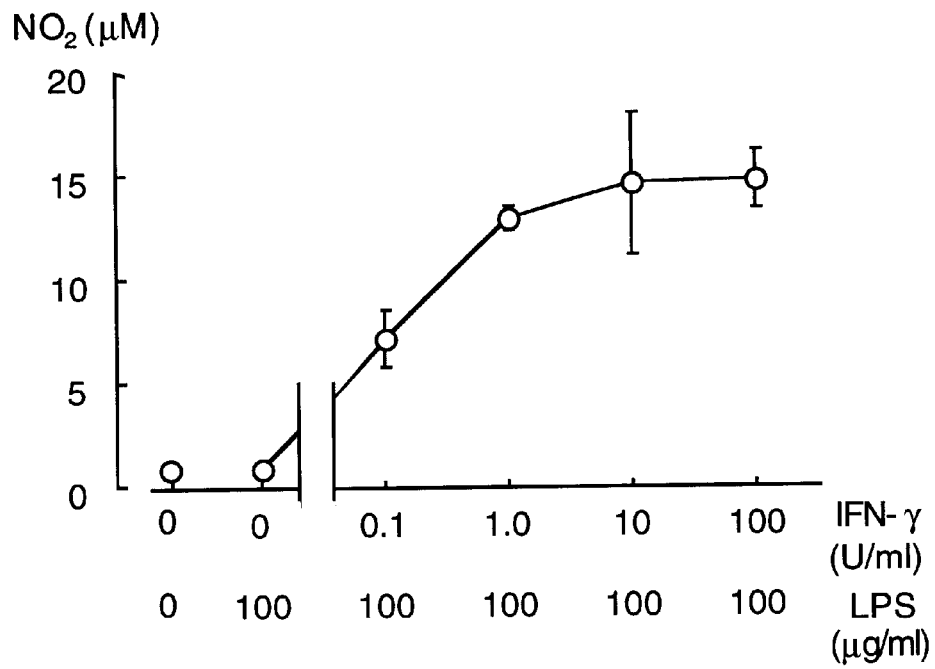
FIG. 4 shows dependence of NO biosynthesis on cytokine concentration and L-arginine availability.

No detectable $NO_2$ was measured in the medium of non-stimulated VSMC. When cells were stimulated with a mixture of IFN-γ (100 U/ml) and LPS (100 μM), a significant amount of $NO_2$ was detected in the medium (14.7±0.3 μM/$10^5$ cells/24 hours). The effect of IFN-γ on NO biosynthesis was dose-dependent (FIG. 4A).

Figure 4B:
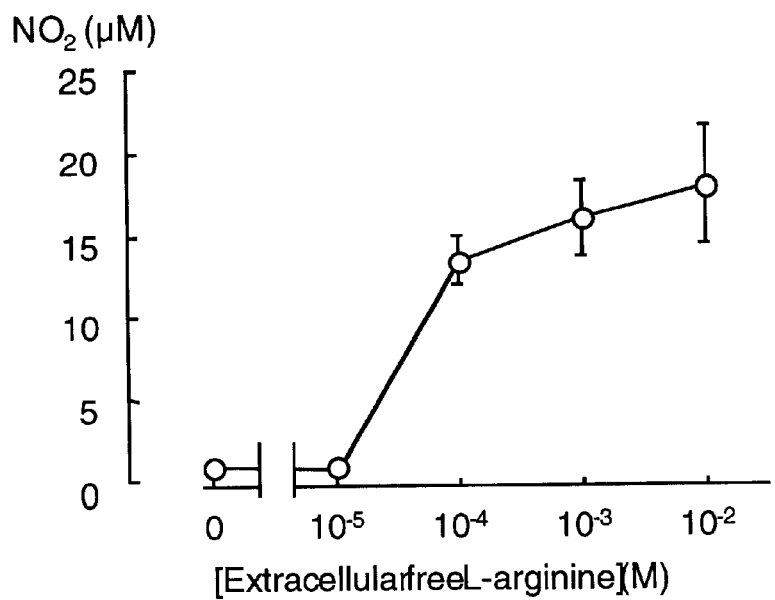

Cells were stimulated with IFN-γ (100 U/ml) and LPS (100 μg/ml) for 24 hours to assess the dose-dependence on substrate availability. Increases in extracellular L-arginine led to a progressive increase in $NO_2$ synthesis by cytokine stimulated VSMC over the range of 0 to 10 mM (FIG. 4B).

Example 6

Effect of Arginine Oligomers on NO Production in VSMC

Subconfluent cells were pre-incubated with medium containing 100 μM arginine for 24 hours. The cells were then transiently pretreated with each arginine polymer for 30 minutes. After translocation, the cells were incubated with a mixture of IFN-γ (100 U/ml) and LPS (100 μg/ml) in medium containing 100 μM L-arginine for another 24 hours. In some experiments, L-NMMA (1 mM), a nitric oxide synthase inhibitor, was added to the medium.

Example 7

Assay for iNOS Protein Expression

In order to clarify the effects of arginine polymer translocation on iNOS expression, iNOS protein concentrations of rat VSMC were analyzed by western blotting. Samples were analyzed from non-stimulated cells, cells stimulated with IFN-γ (100 U/ml) and LPS (100 μg/ml), or R7 (10 μM) pretreated cells which were stimulated with IFN-γ and LPS. Treated cells were washed twice with PBS, and total cell lysates were harvested in 150 μl of lysis buffer containing 150 mM NaCl, 50 mM Tris/Cl, pH 8.0, 1% NP40, and 0.1% SDS. Samples were centrifuged for 5 minutes at 14,000 g, 4° C., to remove insoluble material, and the supernatant was collected. Protein concentrations were measured with the Lowry method. Cell lysates containing 50 μg of protein were boiled for 5 minutes and separated on an 8.0% SDS-polyacrylamide minigel. Eluted proteins were electroblotted onto nitrocellulose membrane (HyBond, Amersham, England). The blots were incubated for 1 hour in 5% non-fat dry milk/0.05% Tween® in Tris buffered saline (TBS) to block non-specific binding of the antibody. Blots were incubated for 3 hours with primary monoclonal antibodies against iNOS protein diluted 1:2,500 in TBS/Tween®. The blots were then incubated with peroxidase labeled gout anti-mouse IgG in the same buffer for 1 hour. Peroxidase labeled protein was visualized with an enhanced chemiluminescence detection system (Amersham, England) on X-ray film.

Example 8

Effect of Treatment with Arginine Oligomers on Vein Graft Segments

A. Surgical Procedure

Male New Zealand white rabbits (3.0–3.5 kg) fed standard diets were anesthetized with a mixture of ketamine (40 mg/kg) and xylazine (5 mg/kg) intramuscularly. The left external jugular vein was exposed through a longitudinal neck incision. The jugular vein was excised, gently flushed and immersed in PBS (control) or PBS containing either L-R7 (10.0 μM) or D-r7 (10.0 μM) for 30 minutes. L-R5 and D-r5 (10.0 μM), which have been previously demonstrated not to translocate across the cell membrane, were used as controls.

The right common carotid artery was exposed and clamped at the both proximal and distal ends. The treated vein segment was washed with PBS and then anastomosed in a reverse end-to-side fashion into the carotid artery, using continuous 8-0 polypropylene sutures. The common carotid artery was ligated and dissected between the two anastomoses, and the wound was closed with 3-0 nylon suture.

B. Vessel Morphometry

Vein graft segments were harvested on the 28th surgical day. Graft segments were fixed in 10% buffered formalin with gentle intraluminal pressure to maintain the physiological graft configuration. The middle portion of the paraffin samples were sectioned (5 μm) and stained with hematoxylin/eosin for light microscopic examination (FIGS. 8A–C). Three sections of each graft, taken at 0.5 mm intervals, were analyzed by planimetry by a observer blinded to the treatment group. The cross-sectional areas of the lumen, intima and media was digitized with the use of the Image Analyst program (Automatrix). The ratio of intima to media (I/M) area was calculated.

Example 9

Ex Vivo NOx Production from Vein Graft

Vein grafts were harvested 3 days after surgery, as described in Example 7. Vein graft segments were incubated in 1 me of Hanks' buffered saline solution (HBSS, Irvine Scientific) containing $Ca^{2+}$ (1.0 mM) and L-arginine (100 μM, Sigma) at 37° C. for 2 hours. NOx (nitrate and nitrite) production was measured either in the absence (basal) or presence (stimulated) of calcium ionophore (A23187, 10.0 μM, Sigma). Samples of the medium (80 μL) were collected, and NOx measurement was performed using the Griess reaction facilitated by a commercial calorimetric assay (Cayman Chemical).

Example 10

VSMC Proliferation Assay

Rat aortic VSMC were grown to 50% confluence in 96-well cell culture plates. VSMC were then washed and incubated with serum free DMEM for 48 hours to obtain quiescent nondividing cells. Thereafter, VSMC were treated with vehicle, L-R7 (10.0 μM), or D-R7 (10.0 μM) for 30 minutes. After the treatment, cells were washed, and further incubated with serum containing DMEM (0.5%, FBS). Cells were harvested after 48 hours of incubation. Cell count was performed with commercial cell proliferation assay kit using spectrophotometer (XTT, Boehringer Mannheim). As a negative control, cells treated with vehicle and incubated with DSF were used. As an index of cell proliferation, the OD ratio of each treatment group to negative control group was calculated as an index of cell proliferation.

Example 11

Heart Transplant Study

PVG rat donor hearts (n=48) were transplanted heterotopically into the abdomen of ACI recipients. Donor hearts received either intracoronary PBS or intracoronary 50 uM (L)-arginine polymer (L-R5 or L-R9) for 30 minutes. Each group was further divided into 60 and 90 day study animals (n=6 each). Tissue cross sections (5μ) were stained with EVG (Elastica-van Gieson) preparation, and vessels were scored using computerized morphometry for analysis of % luminal narrowing, intima to media ratio (I/M), and % affected vessels. Transfection efficiency was determined by infusing biotinylated R5 and R9, as in preceding examples, and calculating the percentage of biotin positive nuclei divided by total number of nuclei. Results are described in Section IV C, above.

While the invention has been described with reference to specific methods and embodiments, it will be appreciated that various modifications and changes may be made without departing from the spirit of the invention.

It is claimed:

1. A method for inhibiting trauma-induced intimal hyperplasia in a graft or vascular vessel receiving a graft, comprising:
contacting a graft, prior to grafting, with a polymer consisting of from 6 to about 30 amino acid subunits in a pharmaceutically acceptable vehicle, wherein at least 50% of said subunits are arginine residues, and said polymer contains at least six contiguous arginine residues.

2. The method of claim 1, wherein at least 70% of the subunits in the polymer are arginine residues.

3. The method of claim 1, wherein at least 90% of the subunits in the polymer are arginine residues.

4. The method of claim 1, wherein no two arginine residues are separated by more than one non-arginine subunit.

5. The method of claim 1, wherein the arginine residues are all L-arginine residues.

6. The method of claim 1, wherein the amino acid subunits other than the arginine residues are natural or unnatural amino acid subunits that do not significantly reduce the rate of membrane transport of the polymer.

7. The method of claim 6, wherein the amino acid subunits other than the arginine residues are selected from the group consisting of glycine, alanine, cysteine, valine, leucine, isoleucine, methionine, serine, threonine, α-amino-β-guanidinopropionic acid, α-amino-γ-guanidinobutyric acid, and α-amino-ε-guanidinocaproic acid.

8. The method of claim 1, wherein said polymer is an arginine homopolymer.

9. The method of claim 8, wherein said polymer is an L-arginine homopolymer.

10. The method of claim 8, wherein said polymer contains 7 to 15 arginine residues.

11. The method of claim 1, wherein the trauma comprises an incision to the graft or vascular vessel receiving a graft, transplant of an organ containing the graft, or a combination thereof.

12. The method of claim 11, wherein the graft is grafted into the vascular vessel.

13. The method of claim 2, wherein the vascular vessel is undergoing a bypass procedure.

14. The method of claim 11, wherein the graft is grafted onto the vascular vessel.

15. The method of claim 14, wherein the vascular vessel is a vein undergoing an arterial venous anastomosis procedure for the purpose of dialysis.

16. The method of claim 11, wherein the graft is contained within a transplanted organ.

17. The method of claim 16, wherein said contacting comprises immersion of the organ in a solution of the polymer.

18. The method of claim 1, wherein the graft is a vascular conduit for a vascular graft procedure, and said contacting is carried out for a time sufficient for the polymer to be transported into the wall of the vascular conduit, such that the level of the polymer in the conduit wall is effective to reduce the level of post-graft intimal hyperplasia in and/or adjacent to the conduit, relative to the level of post-graft intimal hyperplasia that would occur in the absence of such contacting with the polymer.

19. The method of claim 18, wherein said contacting is limited to contacting the polymer-containing liquid with the interior of the vascular conduit.

20. The method of claim 18, wherein the polymer is an arginine homopolymer.

21. The method of claim 20, wherein the polymer is an L-arginine homopolymer.

22. The method of claim 20, wherein the polymer contains 7 to 15 arginine residues.

23. A graft treated according to the method recited in claim 1.

24. The graft of claim 23, wherein the contacting polymer is an arginine homopolymer.

25. The graft of claim 24, wherein the contacting polymer is an L-arginine homopolymer.

26. The graft of claim 24, wherein the contacting polymer contains from 7 to 15 arginine residues.

27. A method of increasing NO production in a graft or vascular vessel receiving a graft, comprising contacting the graft, prior to grafting, with a polymer consisting of from 6 to about 30 amino acid subunits, wherein at least 50% of said subunits are arginine residues, and said polymer contains at least six contiguous arginine residues, in a pharmaceutically acceptable vehicle.

28. The method of claim 27, wherein said polymer is an L-arginine homopolymer containing 7 to 15 L-arginine residues.

* * * * *

UNITED STATES PATENT AND TRADEMARK OFFICE
CERTIFICATE OF CORRECTION

PATENT NO.    : 6,605,115 B1
DATED         : August 12, 2003
INVENTOR(S)   : John P. Cooke et al.

It is certified that error appears in the above-identified patent and that said Letters Patent is hereby corrected as shown below:

Column 22,
Line 3, please delete "2" and insert -- 12 --

Signed and Sealed this

Sixth Day of January, 2004

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,605,115 B1 |
| APPLICATION NO. | : 09/587647 |
| DATED | : August 12, 2003 |
| INVENTOR(S) | : Cooke et al. |

It is certified that error appears in the above-identified patent and that said Letters Patent is hereby corrected as shown below:

Column 1

Line 11, delete "CA 65237" and insert -- CA065237 --
Line 11, delete "may"
Line 12, delete "have" and insert -- has --

Signed and Sealed this

Twenty-second Day of June, 2010

David J. Kappos
*Director of the United States Patent and Trademark Office*